(12) United States Patent
Ishida et al.

(10) Patent No.: US 7,214,817 B2
(45) Date of Patent: May 8, 2007

(54) HYDROXYALKYL (METH)ACRYLATE AND ITS PRODUCTION PROCESS

(75) Inventors: Tokumasa Ishida, Himeji (JP); Hiroyuki Takaki, Himeji (JP); Masahiro Uemura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/436,662

(22) Filed: May 13, 2003

(65) Prior Publication Data

US 2003/0229244 A1 Dec. 11, 2003

(30) Foreign Application Priority Data

Jun. 11, 2002 (JP) ............................... 2002-170516

(51) Int. Cl.
*C07C 67/26* (2006.01)
*C07C 69/73* (2006.01)

(52) U.S. Cl. ....................................... 560/209; 560/183

(58) Field of Classification Search ................ 560/205, 560/209, 183
See application file for complete search history.

(56) References Cited

U.S. PATENT DOCUMENTS

| | | | |
|---|---|---|---|
| 6,380,424 B1 | 4/2002 | Yoneda et al. | |
| 6,414,182 B1 | 7/2002 | Shingai et al. | |
| 6,465,681 B2 * | 10/2002 | Uemura et al. | ............. 560/205 |
| 2002/0040125 A1 * | 4/2002 | Matsumoto et al. | ......... 528/499 |
| 2002/0041025 A1 * | 4/2002 | Matsumoto et al. | ......... 528/499 |
| 2002/0082443 A1 * | 6/2002 | Uemura et al. | ............. 560/209 |

FOREIGN PATENT DOCUMENTS

| | | |
|---|---|---|
| CN | 1293185 A | 5/2001 |
| EP | 1 134 212 A1 | 9/2001 |
| EP | 1 219 588 A2 | 7/2002 |
| JP | 57-38747 A | 3/1982 |
| JP | 10-237022 A | 9/1998 |
| JP | 2001-348362 A | 12/2001 |
| JP | 2003-55304 A | 2/2003 |

* cited by examiner

*Primary Examiner*—Karl Puttlitz

(57) ABSTRACT

The present invention provides: a high-quality hydroxyalkyl (meth)acrylate of which the alkylene glycol di(meth)acrylate content and the acid component content are both low; and its novel production process. The hydroxyalkyl (meth) acrylate, which has a content, in terms of an alkylene glycol di(meth)acrylate as an impurity, of not more than 0.1 weight % and an acid component content of not more than 0.1 weight %, is obtained by a process comprising the step of carrying out a batch reaction between (meth)acrylic acid and an alkylene oxide in the presence of a catalyst in order to produce the hydroxyalkyl (meth)acrylate; with the process making an adjustment as to charging of both raw materials in such a manner that, for, of a time as needed for supplying both raw materials, a supplying time of not less than 40% of a total supplying time when the raw materials as supplied have a temperature of not lower than 40° C., the molar ratio of the integrated amount of the alkylene oxide to the integrated amount of the (meth)acrylic acid that have been added to a reactor by then can be more than 1.0.

5 Claims, No Drawings

＃ HYDROXYALKYL (METH)ACRYLATE AND ITS PRODUCTION PROCESS

BACKGROUND OF THE INVENTION

A. Technical Field

The present invention relates to: a production process for a hydroxyalkyl (meth)acrylate, which comprises the step of carrying out a reaction between (meth)acrylic acid and an alkylene oxide in the presence of a catalyst; and a high-quality hydroxyalkyl (meth)acrylate which is obtained by this process.

B. Background Art

As to production processes for a hydroxyalkyl (meth)acrylate involving the step of carrying out a batch reaction between (meth)acrylic acid and an alkylene oxide in the presence of a catalyst, the following processes have hitherto been common: a process that involves the step of charging a reactor with (meth)acrylic acid and an alkylene oxide (which are raw materials) along with a catalyst in a lump to thus carry out their reaction; and a process that involves the steps of charging a reactor with (meth)acrylic acid (which is a raw material) and a catalyst and thereafter adding an alkylene oxide thereto gradually (continuously or intermittently) at a constant or variable supplying rate to thus carry out their reaction. The reasons therefor are such that: the (meth)acrylic acid has higher catalyst-dissolving ability than the alkylene oxide; and, if the alkylene oxide is initially charged alone into the reactor and then heated, there is involved a danger of explosion, and therefore special facilities for coping with this danger are needed. Even in the former process that involves the step of charging the reactor with the (meth)acrylic acid and the alkylene oxide along with the catalyst in a lump to thus carry out their reaction, strictly the fact is that the (meth)acrylic acid is charged earlier than the alkylene oxide.

However, both in the above processes, there is a problem such that an alkylene glycol di(meth)acrylate (which is a diester and may hereinafter be referred to simply as "diester") and a dialkylene glycol mono(meth)acrylate (which is an alkylene oxide's diaddition product and may hereinafter be referred to simply as "diaddition product") tend to be by-produced as impurities.

Of these by-products, the diaddition product can be removed by distillation, but the diester is difficult to remove even by purification such as distillation, therefore it is important to suppress the diester content at the end of the reaction. In the reaction between the (meth)acrylic acid and the alkylene oxide, the catalyst runs its substitution reaction with the (meth)acrylic acid to form a salt (e.g. chromium (meth)acrylate) to thereby activate the (meth)acrylic acid to thus promote its reaction with the alkylene oxide. However, it is conceived that: the (meth)acrylic acid concentration in the system decreases with the progress of the reaction, whereby the catalyst runs its substitution reaction not with the (meth)acrylic acid but with the formed hydroxyalkyl (meth)acrylate to cause a disproportionation reaction to by-produce the diester. Therefore, when an attempt is made to suppress the side production of the diester in the aforementioned prior processes, there has been adopted a method in which the reaction is early ended in a stage when a lot of (meth)acrylic acid remains unreacted. However, similarly to the diester, the residual acid component is difficult to remove by distillation. Therefore, as to the above method, though the diester content can be decreased, it is inevitable that the acid component content increases with this decrease of the diester content. Incidentally, herein, the acid component means all acids that are contained in the hydroxyalkyl (meth)acrylate and can be measured by neutralization titration.

Thus, as to prior arts, it is difficult to decrease the diester and the acid component at the same time, and it is the present state that, even if only either one of them comes to be contained in a large quantity, the resultant product is so low in purity as to be bad in quality.

SUMMARY OF THE INVENTION

A. Object of the Invention

Thus, an object of the present invention is to provide: a high-quality hydroxyalkyl (meth)acrylate of which the alkylene glycol di(meth)acrylate content and the acid component content are both low; and a novel production process by which this hydroxyalkyl (meth)acrylate can be obtained.

B. Disclosure of the Invention

The present inventors diligently studied to solve the above-mentioned problems. As a result, they have completed the present invention by finding out that, if an adjustment is made in such a manner that the molar ratio between the alkylene oxide and the (meth)acrylic acid (alkylene oxide/(meth)acrylic acid) in the reactor can be more than 1.0 under specific conditions, then the side production of the diester can remarkably be suppressed even though the reaction is run until the amount of the residual acid component in the reactor sufficiently decreases.

That is to say, a hydroxyalkyl (meth)acrylate, according to the present invention, is characterized by having a content, in terms of an alkylene glycol di(meth)acrylate as an impurity, of not more than 0.1 weight % and an acid component content of not more than 0.1 weight %.

A production process for a hydroxyalkyl (meth)acrylate, according to the present invention, comprises the step of carrying out a batch reaction between (meth)acrylic acid and an alkylene oxide in the presence of a catalyst in order to produce the hydroxyalkyl (meth)acrylate; with the production process being characterized by making an adjustment as to charging of both raw materials in such a manner that, for, of a time as needed for supplying both raw materials, a supplying time of not less than 40% of a total supplying time when the raw materials as supplied have a temperature of not lower than 40° C., the molar ratio between the integrated amount of the alkylene oxide and the integrated amount of the (meth)acrylic acid (alkylene oxide/(meth)acrylic acid) that have been added to a reactor by then can be more than 1.0.

These and other objects and the advantages of the present invention will be more fully apparent from the following detailed disclosure.

DETAILED DESCRIPTION OF THE INVENTION

Hereinafter, detailed descriptions are given about the production process for a hydroxyalkyl (meth)acrylate according to the present invention (which may hereinafter be referred to as present invention production process) and the hydroxyalkyl (meth)acrylate according to the present invention. However, the scope of the present invention is not bound to these descriptions. And other than the following illustrations can also be carried out in the form of appropriate modifications of the following illustrations within the scope not departing from the spirit of the present invention.

The present invention production process is a process comprising the step of carrying out batchwise a reaction (carrying out a batch reaction) between the (meth)acrylic acid and the alkylene oxide in the presence of the catalyst in order to obtain the hydroxyalkyl (meth)acrylate. Specifically, for example, it is general that: the catalyst, the (meth)acrylic acid, and the alkylene oxide are appropriately supplied to the reactor to run their reaction, and then, at a point of time when the residual (meth)acrylic acid content of the reaction liquid has decreased to a desired amount, the reaction is ended. Incidentally, this reaction is an exothermic reaction, and begins at a point of time when the (meth) acrylic acid and the alkylene oxide have come to coexist at a predetermined reaction temperature in the presence of the catalyst, and then this reaction is ended by dropping the temperature of the reaction liquid to lower than the set predetermined reaction temperature by such as cooling.

Though not especially limited, the alkylene oxide usable in the present invention production process is favorably an alkylene oxide having 2 to 6 carbon atoms, more favorably 2 to 4 carbon atoms. Specific examples thereof include ethylene oxide, propylene oxide, and butylene oxide. Of these, the ethylene oxide and the propylene oxide are particularly favorable. In addition, the (meth)acrylic acid usable in the present invention means acrylic acid and/or methacrylic acid. Incidentally, in the present invention and the present specification, as to the hydroxyalkyl (meth) acrylate (which is the objective product) and as to the alkylene glycol di(meth)acrylate and the dialkylene glycol mono(meth)acrylate as by-products and impurities, the "(meth)acrylate" portion of these compounds' names is defined as having two meanings of "acrylate" and "methacrylate", in detail, as follows: when the above (meth)acrylic acid (which is a raw material) is acrylic acid, the "(meth) acrylate" is defined as meaning "acrylate" in derivation from the acrylic acid; and, when the above (meth)acrylic acid (which is a raw material) is methacrylic acid, the "(meth) acrylate" is defined as meaning "methacrylate" in derivation from the methacrylic acid.

As to quantitative relations between the amount of the entire (meth)acrylic acid to be supplied and the amount of the entire alkylene oxide to be supplied in the present invention production process, the amount of the alkylene oxide is favorably in the range of 1.0 to 10 mols, more favorably 1.0 to 5.0 mols, still more favorably 1.0 to 3.0 mols, particularly favorably 1.0 to 2.0 mols, per 1 mol of the (meth)acrylic acid. In the case where the amount of the alkylene oxide is smaller than 1.0 mol per 1 mol of the (meth)acrylic acid, there is a possibility that the reaction may be difficult to run. On the other hand, in the case where the amount of the alkylene oxide is larger than 10 mols per 1 mol of the (meth)acrylic acid, there is a possibility that: such as the step of recovering the alkylene oxide may be needed and therefore inflict an economical loss.

In the present invention production process, it is important to make an adjustment as to charging of both raw materials (the (meth)acrylic acid and the alkylene oxide) in such a manner that, for, of a time as needed for supplying both raw materials, a supplying time of not less than 40% of a total supplying time when the raw materials as supplied have a temperature of not lower than 40° C., the molar ratio between the integrated amount of the alkylene oxide and the integrated amount of the (meth)acrylic acid (alkylene oxide/ (meth)acrylic acid) that have been added to a reactor by then can be more than 1.0. Thereby the side production of the diester can remarkably be suppressed even though the reaction is run until the amount of the residual acid component in the reaction liquid sufficiently decreases, therefore it becomes possible to decrease both the diester content and the acid component content. Furthermore, the diester is a substance to promote the polymerization of the hydroxyalkyl (meth)acrylate, therefore the polymerization of the hydroxyalkyl (meth)acrylate, which may occur during the reaction, can also be suppressed by the suppression of the side production of the diester, and effects can also be expected such that the clogging due to the polymerization in the reactor and the piping can be avoided.

In the present invention production process, of the time as needed for supplying both raw materials, the total supplying time when the raw materials as supplied have a temperature of not lower than 40° C. is, in other words, a total time as needed for the supply when the alkylene oxide and/or the (meth)acrylic acid are supplied into the reactor when the raw materials (reaction liquid) that have been added into the reactor by then have a temperature-of not lower than 40° C. (if there are a time to simultaneously supply both the alkylene oxide and the (meth)acrylic acid and a time to supply only one of them, then their total time is the abovementioned total supplying time). In addition, if a raw material as beforehand heated to not lower than 40° C. is supplied into the reactor, then it is prescribed that the time as needed for this supply should also be included in the total supplying time when the raw materials as supplied have a temperature of not lower than 40° C.

In the present invention production process, favorably, the adjustment of the aforementioned molar ratio (alkylene oxide/(meth)acrylic acid) into the aforementioned range is made for, of the time as needed for supplying both raw materials, desirably a supplying time of not less than 60% of the total supplying time when the raw materials as supplied have a temperature of not lower than 40° C., and more favorably the above adjustment is made desirably for the total supplying time when the raw materials as supplied have a temperature of not lower than 40° C. In addition, even if the raw materials as supplied have a temperature of lower than 40° C., it is desirable to adjust the aforementioned molar ratio (alkylene oxide/(meth)acrylic acid) so as to be in the aforementioned range. In a more favorable mode, it is good to adjust the aforementioned molar ratio (alkylene oxide/(meth)acrylic acid) so as to be in the aforementioned range for a supplying time of not less than 40%, still more favorably not less than. 60%, yet still more favorably 100%, of the total supplying time when the raw materials as supplied have a temperature of not lower than 20° C. In the most favorable mode, it is good to adjust the aforementioned molar ratio (alkylene oxide/(meth)acrylic acid) so as to be in the aforementioned range since a point of time when the catalyst, the (meth)acrylic acid, and the alkylene oxide have come to coexist in the reactor.

In the present invention production process, there is no especial limitation on the manner (order) of charging the raw (meth)acrylic acid and the raw alkylene oxide, if it is a charging manner such that the aforementioned molar ratio (alkylene oxide/(meth)acrylic acid) can be more than 1.0 for the aforementioned specific time. For example, it is permitted that: a portion or the entirety of the (meth)acrylic acid is initially charged into the reactor, and then thereto there is supplied the alkylene oxide or there are supplied the alkylene oxide and the rest of the (meth)acrylic acid.

Above all, in the present invention, it is favorable to begin to supply the (meth)acrylic acid after having charged the alkylene oxide and/or the hydroxyalkyl (meth)acrylate into the reactor. In other words, it is favorable that: in the initially charging step, the raw (meth)acrylic acid is not beforehand charged, but the alkylene oxide (raw material) and/or the hydroxyalkyl (meth)acrylate (objective product) are charged; and at least the (meth)acrylic acid begins to be supplied after the above initially charging step. Specifically, in the case where the alkylene oxide is initially charged or where the alkylene oxide and the hydroxyalkyl (meth) acrylate are initially charged, it is favorable to begin to supply the (meth)acrylic acid after the above initially charging; or, if a portion of the amount of the alkylene oxide is initially charged, to begin to supply the (meth)acrylic acid and the residual alkylene oxide after the above initially charging. In addition, in the case where the hydroxyalkyl (meth)acrylate is initially charged, it is favorable to begin to supply the (meth)acrylic acid and the alkylene oxide after the above initially charging.

In the above case where the alkylene oxide and/or the hydroxyalkyl (meth)acrylate are initially charged, as to the amount of the alkylene oxide as initially charged, it is enough if all or a portion of the amount of the entire alkylene oxide to be supplied is charged, and as to the amount of the hydroxyalkyl (meth)acrylate as initially charged, it is enough if a product or a reaction liquid as obtained in the previously performed reaction is charged in the range of not more than 20 vol % of the capacity of the reactor. Thereby the aforementioned molar ratio (alkylene oxide/(meth) acrylic acid) can easily be adjusted so as to be more than 1.0. In addition, in the charging method as hitherto commonly carried out in which the (meth)acrylic acid is initially charged into the reactor, it is impossible to take the mode, as aforementioned as the most favorable mode, in which the aforementioned molar ratio (alkylene oxide/(meth)acrylic acid) is adjusted so as to be more than 1.0 since a point of time when the catalyst, the (meth)acrylic acid, and the alkylene oxide have come to coexist in the reactor. However, in the above charging method, there are also advantages such that the aforementioned most favorable mode becomes possible by arranging that the raw material as charged earlier should be not the (meth)acrylic acid but the alkylene oxide. Incidentally, the reason why the hydroxyalkyl (meth)acrylate (objective product) is initially charged is that its purpose is to enhance the solubility of the catalyst. However, in the case where only the alkylene oxide is initially charged, even if the catalyst is in a not entirely dissolved state in the initially charging step, there is no problem, because the catalyst can be dissolved gradually with the subsequent supply of the (meth)acrylic acid.

In the present invention production process, as to the charging of both raw materials, in the case where there is included a stage when the molar ratio between the integrated amount of the alkylene oxide and the integrated amount of the (meth)acrylic acid (alkylene oxide/(meth)acrylic acid) that have been added into the reactor is not more than 1.0, it is favorable to make an adjustment in such a manner that, during this stage, the total of the integrated amount of the alkylene oxide and the integrated amount of the (meth) acrylic acid that have been added into the reactor by then may not be more than 60 weight %, more favorably may not be more than 50 weight %, of the total of the amount of the entire alkylene oxide and the amount of the entire (meth) acrylic acid that are to be supplied by the end of the reaction. In the stage when the aforementioned molar ratio (alkylene oxide/(meth)acrylic acid) is not more than 1.0, the diester comparatively tends to form as a by-product, but, if the total of the amount of the alkylene oxide as added and the amount of the (meth)acrylic acid as added is adjusted so as to be in the aforementioned range during this stage, then the side production of the diester can more effectively be suppressed.

In the case where the total of the amount of the alkylene oxide as added and the amount of the (meth)acrylic acid as added is more than 60 weight % of the total of the amount of the entire alkylene oxide to be supplied and the amount of the entire (meth)acrylic acid to be supplied, there is a possibility that the diester cannot sufficiently be suppressed.

In the present invention production process, the aforementioned charging (supply) of the (meth)acrylic acid and the alkylene oxide may be either lump-sum addition or gradual addition (continuous and/or intermittent addition), but favorably, their initially charged portions are added in a lump, and their subsequently supplied portions are added gradually. Incidentally, the continuous addition means a mode such that the material is continuously added little by little, and the intermittent addition means a mode such that the material is pulsewise or intermittently added divisionally into any number of times. Moreover, in the case where the addition is continuously carried out, the continuous addition may be run with the addition rate kept constant until the end of the addition, or may be run with the addition rate changed at least once on the way, or may be run while the rate itself is varied continuously and arbitrarily. However, in the case of changing the rate on the way, it is favorable to reduce the rate from that before the change to that after the change.

Moreover, when the (meth)acrylic acid and the alkylene oxide are added, they may be added at ordinary temperature or after having beforehand be heated to a desirable temperature so as not to change an internal temperature which the system has at that point of time.

Moreover, in the case where both the (meth)acrylic acid and the alkylene oxide are simultaneously added, they may be added from their respective different addition lines, or they may be added after having beforehand been mixed together by using such as piping, a line mixer, or a mixing tank before being added to the reactor. However, in the case of the addition from their respective different addition lines, there is a possibility that the molar ratio between the alkylene oxide and the (meth)acrylic acid may be distributed unevenly in the system, therefore it is favorable that the above raw materials are added after having beforehand been mixed together before being added to the reactor. Incidentally, in the case where the raw materials are added from their respective different addition lines, they do not necessarily need to be the same as to such as the modes of the addition (lump-sum addition, gradual addition), the temperatures of the raw materials as added, and the addition rate.

Incidentally, in the present invention production process, the time, as needed for finishing charging the amount of the entire (meth)acrylic acid to be supplied and the amount of the entire alkylene oxide to be supplied, is not especially limited, but may be set appropriately in consideration of such as: how the reaction is coming along; and the productivity.

There is no especial limitation on the catalyst usable in the present invention production process. However, specific favorable examples thereof include catalysts including at least one member selected from the group consisting of: chromium (Cr) compounds, iron (Fe) compounds, yttrium (Y) compounds, lanthanum (La) compounds, cerium (Ce) compounds, tungsten (W) compounds, zirconium (Zr) compounds, titanium (Ti) compounds, vanadium (V) compounds, phosphorus (P) compounds, aluminum (Al) compounds, molybdenum (Mo) compounds, and amine compounds; and homogeneous catalysts are more favorable. In particular, if the amine compound and another catalyst are used together as catalysts, there are obtained effects such that: the synergistic effect is seen as to the catalytic activity, and the reaction conversion is enhanced, and further the reaction selectivity is also enhanced.

There is no especial limitation on the aforementioned chromium (Cr) compound if it is a compound containing a chromium (Cr) atom in its molecule and is soluble in the reaction liquid. Specific examples thereof include chromium chloride, chromium acetylacetonate, chromium formate, chromium acetate, chromium acrylate, chromium methacrylate, sodium bichromate, and chromium dibutyldithiocarbamate.

There is no especial limitation on the aforementioned iron (Fe) compound if it is a compound containing an iron (Fe) atom in its molecule and is soluble in the reaction liquid. Specific examples thereof include iron powders, iron chloride, iron formate, iron acetate, iron acrylate, and iron methacrylate.

There is no especial limitation on the aforementioned yttrium (Y) compound if it is a compound containing an yttrium (Y) atom in its molecule and is soluble in the reaction liquid. Specific examples thereof include yttrium acetylacetonate, yttrium chloride, yttrium acetate, yttrium nitrate, yttrium sulfate, yttrium acrylate, and yttrium methacrylate.

There is no especial limitation on the aforementioned lanthanum (La) compound if it is a compound containing a lanthanum (La) atom in its molecule and is soluble in the reaction liquid. Specific examples thereof include lanthanum acetylacetonate, lanthanum chloride, lanthanum acetate, lanthanum nitrate, lanthanum sulfate, lanthanum acrylate, and lanthanum methacrylate.

There is no especial limitation on the aforementioned cerium (Ce) compound if it is a compound containing a cerium (Ce) atom in its molecule and is soluble in the reaction liquid. Specific examples thereof include cerium acetylacetonate, cerium chloride, cerium acetate, cerium nitrate, cerium sulfate, cerium acrylate, and cerium methacrylate.

There is no especial limitation on the aforementioned tungsten (W) compound if it is a compound containing a tungsten (W) atom in its molecule and is soluble in the reaction liquid. Specific examples thereof include tungsten chloride, tungsten acrylate, and tungsten methacrylate.

There is no especial limitation on the aforementioned zirconium (Zr) compound if it is a compound containing a zirconium (Zr) atom in its molecule and is soluble in the reaction liquid. Specific examples thereof include zirconium acetylacetonate, zirconium chloride, zirconium acetate, zirconium nitrate, zirconium sulfate, zirconium acrylate, zirconium methacrylate, zirconium butoxide, zirconium propoxide, zirconyl chloride, zirconyl acetate, zirconyl nitrate, zirconyl acrylate, and zirconyl methacrylate.

There is no especial limitation on the aforementioned titanium (Ti) compound if it is a compound containing a titanium (Ti) atom in its molecule and is soluble in the reaction liquid. Specific examples thereof include titanium chloride, titanium nitrate, titanium sulfate, titanium methoxide, titanium ethoxide, titanium propoxide, titanium isopropoxide, titanium acrylate, and titanium methacrylate.

There is no especial limitation on the aforementioned vanadium (V) compound if it is a compound containing a vanadium (V) atom in its molecule and is soluble in the reaction liquid. Specific examples thereof include vanadium acetylacetonate, vanadium chloride, vanadium naphthenate, vanadium acrylate, and vanadium methacrylate.

There is no especial limitation on the aforementioned phosphorus (P) compound if it is a compound containing a phosphorus (P) atom in its molecule and is soluble in the reaction liquid. Specific examples thereof include: alkylphosphines, such as trimethylphosphine, tributylphosphine, trioctylphosphine, triphenylphosphine, tritolylphosphine, and 1,2-bis(diphenylphosphine)ethane; and their quaternary phosphonium salts such as (meth)acrylate salts.

There is no especial limitation on the aforementioned aluminum (Al) compound if it is a compound containing an aluminum (Al) atom in its molecule and is soluble in the reaction liquid. Specific examples thereof include aluminum acetylacetonate, aluminum chloride, aluminum acetate, aluminum nitrate, aluminum sulfate, aluminum ethoxide, aluminum isopropoxide, aluminum acrylate, and aluminum methacrylate.

There is no especial limitation on the aforementioned molybdenum (Mo) compound if it is a compound containing a molybdenum (Mo) atom in its molecule and is soluble in the reaction liquid. Specific examples thereof include molybdenum chloride, molybdenum acetate, molybdenum acrylate, and molybdenum methacrylate.

There is no especial limitation on the aforementioned amine compound if it is a compound containing an amine functional group in its molecule. Specific examples thereof include: homogeneous amine compounds, such as trialkylamines, cyclic amines (e.g. pyridine), and their quaternary salts; and heterogeneous amine compounds, such as basic anion-exchange resins containing at least one kind of basic functional group (e.g. a tertiary amino group, a quaternary ammonium group, and a pyridinium group). The amine compound is favorably the basic anion-exchange resin containing at least one kind of basic functional group (e.g. a tertiary amino group, a quaternary ammonium group, and a pyridinium group), and is more favorably a basic anion-exchange resin containing at least one kind of functional group selected from the group consisting of tertiary amino groups, quaternary ammonium groups, and pyridinium groups.

In addition, in the case where a metal-ion-containing homogeneous metal catalyst such as metal salt and metallic complex (e.g. chromium compounds, iron compounds) is used as the aforementioned catalyst, it becomes possible to recover the used catalyst, and it is also possible to recycle the recovered catalyst. Generally, if the amount of the forming diester (which is a by-product) increases, there is a possibility of deactivating the catalyst. However, in the present invention production process, because the side production of the diester can sufficiently be suppressed, the recovery and recycling of the catalyst can effectively be carried out. As to the recycling of the catalyst, specifically, for example, if the reaction is carried out in the coexistence of an anion-exchange resin (basic anion-exchange resin containing at least one kind of basic functional group (e.g. a quaternary phosphonium salt, a tertiary amino group, a quaternary ammonium group, and a pyridinium group)) with a metal-ion-containing homogeneous metal catalyst (e.g. a metal salt and a metallic complex), then the anion-exchange resin can be caused to adsorb the homogeneous metal catalyst with the progress of the reaction (specifically, the homogeneous metal catalyst can be adsorbed when the concentration of the (meth)acrylic acid in the reaction liquid has decreased to approximately 0.10 weight %). Therefore, it is enough if the adsorbed homogeneous metal catalyst is freed by bringing the raw (meth)acrylic acid into contact with the anion-exchange resin having adsorbed this homogeneous metal catalyst.

There is no especial limitation on the amount of the aforementioned catalyst as used in the present invention production process. However, in the case of the homogeneous catalyst, it is favorably used in the range of 0.001 to 10 mol %, more favorably 0.005 to 5 mol %, still more favorably 0.01 to 3 mol %, relative to the amount of the entire raw (meth)acrylic acid to be supplied. In the case where the amount of the aforementioned catalyst is smaller than 0.001 mol %, there is a possibility that: the reaction rate may be so slow that the reaction time may be so long as to result in low productivity. On the other hand, in the case where the amount of the aforementioned catalyst is larger than 10 mol %, there are disadvantages in that the reaction selectivity of the by-product tends to be high. On the other hand, in the case of the heterogeneous catalyst, there is no especial limitation on the amount of the catalyst as used. However, it is favorably used in the range of 5 to 80 weight %, more favorably 10 to 70 weight %, relative to the amount of the entire raw (meth)acrylic acid to be supplied. In addition, even if the amount of the catalyst is small, there is not spoiled the diester-suppressing effect of the present invention. Therefore, from the viewpoint of reducing the side production of impurities derived from the catalyst, the smaller in the aforementioned range the amount of the catalyst as used is, the more favorable it is. Incidentally, there is no especial limitation on the impurities derived from the catalyst. However, specific examples thereof include hydroxyalkyl acetates (e.g. hydroxyethyl acetate and hydroxypropyl acetate) in the case of using the chromium acetate as the catalyst.

In the present invention production process, as to the aforementioned catalyst, it is general that the amount of its entirety to be used is beforehand charged to the reactor. However, there is no limitation thereto. For example, it is permitted that: a portion of the amount of the entire catalyst to be used is initially charged to the reactor, and then the residual portion is additionally supplied on the way of the progress of the reaction. In addition, in the case where the aforementioned catalyst is the homogeneous catalyst, it may be charged or supplied into the reactor after having beforehand been dissolved into either of both raw materials and, for example, in the case where it is initially charged, it may be charged into the reactor after having beforehand been dissolved into the raw materials (as initially charged) (which are favorably the alkylene oxide and/or the hydroxyalkyl (meth)acrylate, but may further include a predetermined amount of (meth)acrylic acid) in a dissolution tank different from the reactor.

In the present invention production process, a polymerization inhibitor may be added into the system during the reaction, if necessary. There is no especial limitation on the polymerization inhibitor, and any one is usable if it is a polymerization inhibitor as commonly industrially used. Specific examples thereof include: phenol compounds, such as hydroquinone, methylhydroquinone, tert-butylhydroquinone, 2,6-di-tert-butylhydroquinone, 2,5-di-tert-butylhydroquinone, 2,4-dimethyl-6-tert-butylphenol, and hydroquinone monomethyl ether; p-phenylenediamines, such as N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N,N'-diphenyl-p-phenylenediamine, and N,N'-di-2-naphthyl-p-phenylenediamine; amine compounds, such as thiodiphenylamine and phenothiazine; copper dialkyldithiocarbamates, such as copper dibutyldithiocarbamate, copper diethyldithiocarbamate, and copper dimethyldithiocarbamate; and N-oxyl compounds, such as 2,2,4,4-tetramethylazetidine-1-oxyl, 2,2-dimethyl-4,4-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5)decane-6-oxyl, 2,2,6,6-tetramethyl-4-acetoxypiperidine-1-oxyl, 2,2,6,6-tetramethyl-4-benzoyloxypiperidine-1-oxyl, and 4,4',4''-tris-(2,2,6,6-tetramethylpiperidine-1-oxyl) phosphite. These polymerization inhibitors may be used either alone respectively or in combinations with each other.

In the case where the aforementioned polymerization inhibitor is used, the amount of it as added is favorably in the range of 0.0001 to 1 weight %, more favorably 0.001 to 0.5 weight %, relative to the amount of the entire raw (meth)acrylic acid to be supplied. Moreover, as to when to add the polymerization inhibitor, although there is no especial limitation, yet it is favorable to initially add it into the reactor together with components as initially charged.

In the present invention production process, the reaction may be carried out in the presence of a solvent, within such a range as does not spoil the effects of the present invention, for the purpose of such as mildly running the reaction. Usable as the solvent is, for specific example, at least one of conventional solvents such as toluene, xylene, heptane, and octane.

In the present invention production process, the temperature of the reaction between the (meth)acrylic acid and the alkylene oxide is usually in the range of favorably 40 to 120° C., more favorably 50 to 120° C., still more favorably 50 to 110° C., particularly favorably 50 to 100° C. In the case where the reaction temperature is lower than 40° C., the reaction rate tends to remarkably decrease to prolong the reaction time, thus resulting in low productivity. On the other hand, in the case where the reaction temperature is higher than 120° C., there is a possibility that the diester or the diaddition product may easily be by-produced.

Incidentally, in the present invention production process, it is possible to suppress the side production of the diester regardless of reaction temperature, but, for more effectively suppressing it, it is favorable that the reaction temperature is set to be in the range lower than the above-mentioned usual reaction temperature range by not less than 5° C., more favorably by 5 to 50° C., still more favorably by 10 to 30° C. In the case where the reaction temperature is lower than the above-mentioned usual reaction temperature range by more than 50° C., the diaddition product tends to easily be by-produced, and also there is a possibility that the reaction time may be prolonged so much as to result in low productivity.

In the present invention production process, the pressure inside the system during the reaction depends on kinds and ratios of raw materials used, but generally the reaction is favorably carried out under pressure.

In the present invention production process, it may be judged that the end time of the reaction is a point of time when the unreacted (meth)acrylic acid remaining in the system has sufficiently disappeared. Specifically, it is favorable to stop the reaction at a point of time when the unreacted (meth)acrylic acid has decreased to not more than 0.2 weight %, more favorably not more than 0.1 weight %. Incidentally, for stopping the reaction, it is enough to rapidly drop the temperature of the reaction liquid from the aforementioned reaction temperature by such as cooling. In the present invention production process, because the side production of the diester can efficiently be suppressed, the reaction can be run until the unreacted (meth)acrylic acid sufficiently disappears. In addition, thereby there can be obtained a product having an extremely low acid component content.

In the present invention production process, after the end of the reaction, it is enough that: the unreacted alkylene oxide is removed by such an -operation as conventionally carried out in this kind of reaction, and then the purification is carried out by conventional methods such as distillation, thus obtaining the objective hydroxyalkyl (meth)acrylate. Specifically, it is enough that: the alkylene oxide remaining unreacted is removed under vacuum, and then the distillation is carried out, for example, under a pressure of 1 to 50 hPa, favorably 1 to 20 hPa, at a temperature of 50 to 120° C., favorably 60 to 100° C.

In the present invention production process, it is favorable to add a diester inhibitor after the end of the reaction. Thereby, the side production of the diester which makes progress after the end of the reaction can also effectively be inhibited to further decrease the diester. Specific examples of the diester inhibitor include: carboxylic acids and carboxylic anhydrides, such as oxalic acid, oxalic anhydride, malonic acid, succinic acid, succinic anhydride, fumaric acid, maleic acid, maleic anhydride, salicylic acid, octanoic acid, adipic acid, sebacic acid, tetradecanedicarboxylic acid, 1,2,4-butanetricarboxylic acid, 1,3,6-hexanetricarboxylic acid, 1,2,3,4-butanetetracarboxylic acid, 1,2,3,4-pentanetetracarboxylic acid, 1,6,7,12-dodecanetetracarboxylic acid, benzoic acid, o-toluic acid, m-toluic acid, p-toluic acid, phthalic acid, phthalic anhydride, isophthalic acid, terephthalic acid, 2,6-naphthalenedicarboxylic acid, pyromellitic acid, pyromellitic anhydride, trimellitic acid, trimellitic anhydride, 1,2,4-benzenetricarboxylic acid, 1,4,5,8-naphthalenetetracarboxylic acid, 1,3,5,7-naphthalenetetracarboxylic acid, and poly(acrylic acid); polyhydric alcohols, such as glycerol, diethylene glycol, trimethylolpropane, cresol, 1,2,6-hexanetriol, pentaerythritol, dipentaerythritol, 2,3,4,5-tetrahydroxyhexane, xylitol, mannitol, catechol, resorcin, 2,6-dihydroxytoluene, tert-butylcatechol, pyrogallol, 2,4-bis(hydroxymethyl)phenol, 1,2,4-trihydroxybenzene, 1,3,5-trihydroxybenzene, 2,4,6-tris(hydroxymethyl)phenol, and 1,2,4,5-tetrahydroxybenzene; and metal-chelating agents, such as ethylenediaminetetraacetic acid, ethylenediaminetetrapropionic acid, nitrilotriacetic acid, iminodiacetic acid, 1,2-diaminocyclohexanetetraacetic acid, acetylacetone, cupferron, oxine, benzidine, and diethyldithiocarbamic acid. These diester inhibitors may be used either alone respectively or in combinations with each other.

In the case where the aforementioned diester inhibitor is used, the amount of it as added is favorably in the range of 0.1 to 10 mols, more favorably 0.5 to 5 mols, per 1 mol of the aforementioned catalyst. In the case where-the above amount is smaller than 0.1 mol per 1 mol of the catalyst, there is a possibility that the effect of inhibiting the side production of the diester may not sufficiently be displayed. On the other hand, in the case where the above amount is larger than 10 mols, there is a possibility that the added diester inhibitor may deteriorate the product purity and, particularly when the carboxylic acid is used, there is a possibility that the acid component content of the resultant product may increase. Moreover, as to when to add the diester inhibitor, there is no especial limitation if it is later than the end of the reaction. For example, it is enough if the diester inhibitor is added all at once or divisionally into at least two times, for example, immediately after the stop of the reaction (the beginning of the cooling), or at the beginning of the distillation, or during the distillation. However, it is favorable to add it immediately after the stop of the reaction.

The hydroxyalkyl (meth)acrylate, according to the present invention, has a content, in terms of an alkylene glycol di(meth)acrylate as an impurity, of not more than 0.1 weight % and an acid component content of not more than 0.1 weight %. The hydroxyalkyl (meth)acrylate according to the present invention, of which the diester content and the acid component content are both low in this way, can easily be obtained by the aforementioned present invention production process. In detail, commonly, the hydroxyalkyl (meth)acrylate is different, according to its kind (kinds and combination of the (meth)acrylic acid and the alkylene oxide as used during the production), about the easiness of the side production of the diester and also about the achievable levels of the diester content and acid component content. However, in the present invention production process, at least the levels in the aforementioned range (such that neither the diester content nor the acid component content is more than 0.1 weight %) can be achieved regardless of the kind of the hydroxyalkyl (meth)acrylate.

Though not especially limited, examples of the hydroxyalkyl (meth)acrylate according to the present invention include: hydroxyethyl acrylate and hydroxypropyl acrylate in the case where acrylic acid is used as the raw (meth)acrylic acid; and hydroxyethyl methacrylate and hydroxypropyl methacrylate in the case where methacrylic acid is used as the raw (meth)acrylic acid.

In the present invention, the hydroxyethyl acrylate which is obtained by a process including the step of carrying out a reaction between acrylic acid and ethylene oxide is one of favorable modes. Its reason is that: the diester is. easily by-produced particularly in this reaction between acrylic acid and ethylene oxide, and it is therefore very difficult to decrease both the diester content and the acid component content into the aforementioned range (such that neither the diester content nor the acid component content is more than 0.1 weight %), but the present invention can easily achieve this.

In the case where the hydroxyalkyl (meth)acrylate according to the present invention is a product (hydroxyalkyl methacrylate) obtained by a process including the step of carrying out a reaction between methacrylic acid and the alkylene oxide, it is favorable that: the content in terms of the alkylene glycol di(meth)acrylate as a by-product and impurity (i.e. alkylene glycol dimethacrylate) is not more than 0.08 weight %, and the acid component content is not more than 0.04 weight %. In the reaction between the methacrylic acid and the alkylene oxide, the side production of the diester is comparatively little. Therefore, in the case of the hydroxyalkyl methacrylate, the present invention production process can achieve severer levels than the aforementioned range (such that neither the diester content nor the acid component content is more than 0.1 weight %).

The diester content and the acid component content in the hydroxyalkyl (meth)acrylate according to the present invention are more favorably as follows: in the case of the hydroxyalkyl acrylate (in the case where acrylic acid is used as the raw (meth)acrylic acid), the diester content is not more than 0.08 weight %, and the acid component content is not more than 0.1 weight %; and on the other hand, in the case of the hydroxyalkyl methacrylate (in the case where methacrylic acid is used as the raw (meth)acrylic acid), the diester content is not more than 0.05 weight %, and the acid component content is not more than 0.04 weight %. The hydroxyalkyl (meth)acrylate, of which the diester content and the acid component content are in the more favorable ranges in this way, can easily be obtained by applying the more favorable mode (such as use of the diester inhibitor) in the aforementioned production process.

As to the hydroxyalkyl (meth)acrylate according to the present invention, the diester content and the acid component content are both extremely low. Therefore, for example, also in uses such that the amount of the hydroxyalkyl (meth)acrylate as used has hitherto been restricted in order to avoid the gelation caused by the diester (which is a substance to promote the polymerization) or to avoid troubles (e.g. coloring) caused by the acid component, it becomes possible to use the hydroxyalkyl (meth)acrylate in such an amount as can sufficiently display the effects of the hydroxyalkyl (meth)acrylate without concern about the above demerits. The hydroxyalkyl (meth)acrylate according to the present invention can, specifically, for example, be used suitably for uses such as: acrylic coatings used for such as automobile topcoat; and pressure sensitive adhesives.

(Effects and Advantages of the Invention):

The present invention can provide: a high-quality hydroxyalkyl (meth)acrylate of which the alkylene glycol di(meth)acrylate content and the acid component content are both low; and a novel production process by which this hydroxyalkyl (meth)acrylate can easily be obtained.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to them in any way. Incidentally, hereinafter, for convenience, the unit "liter(s)" may be referred to simply as "L".

EXAMPLE 1

An SUS-316-made autoclave of 1 L in capacity with a stirrer was charged with 282 g of ethylene oxide, 2.10 g of chromium acetate (as a catalyst), and 0.42 g of phenothiazine (as a polymerization inhibitor), and then internal air of the autoclave was replaced with nitrogen gas, and then the temperature was raised to 60° C. and the internal pressure was adjusted to 1.0 MPa. Next, 420 g of acrylic acid was supplied at an almost constant rate over a period of 2 hours (during this supply, the molar ratio of ethylene oxide/acrylic acid was set at not less than 1.1 and, after the end of the supply, this ratio was 1.1), while 60° C. was kept to carry out a reaction. After the supply of the acrylic acid had been completed, the reaction temperature was kept constant at 60° C. to continue the reaction till the amount of the unreacted acrylic acid (measured by neutralization titration) decreased to 0.10 weight %. As a result of the continuation of the reaction for 4.5 hours, the unreacted acrylic acid decreased to 0.10 weight %, so the reaction liquid was cooled. A gas-chromatographic analysis of the resultant reaction liquid showed a hydroxyethyl acrylate (objective product) concentration of 91 weight %, an ethylene glycol diacrylate (diester) concentration of 0.09 weight %, and a diethylene glycol monoacrylate (diaddition product) concentration of 7.2 weight %.

Next, the resultant reaction liquid was transferred into a glass round-bottom flask of 1 L in capacity, as set to a vacuum distillation apparatus, to carry out purification by distillation under a vacuum of 2 to 10 hPa in the internal temperature range of 60 to 100° C. while the reaction liquid was caused to bubble with air at 10 mL/min, thus obtaining 626 g of hydroxyethyl acrylate.

A gas-chromatographic analysis of the resultant hydroxyethyl acrylate showed its purity of 97.0 weight % and an ethylene glycol diacrylate (impurity) content of 0.10 weight %, and an analysis by neutralization titration showed an acid component content of 0.06 weight %.

EXAMPLE 2

The reaction was carried out in the same way as of Example 1, and then 0.8 g of maleic acid was added as a diester inhibitor to the resultant reaction liquid. Thereafter, the purification was carried out in the same way as of Example 1, thus obtaining 626 g of hydroxyethyl acrylate.

A gas-chromatographic analysis of the resultant hydroxyethyl acrylate showed its purity of 97.0 weight % and an ethylene glycol diacrylate (impurity) content of 0.06 weight %, and an analysis by neutralization titration showed an acid component content of 0.06 weight %.

EXAMPLE 3

An SUS-316-made autoclave of 1 L in capacity with a stirrer was charged with 140 g of hydroxyethyl acrylate, 2.10 g of chromium acetate (as a catalyst), and 0.42 g of phenothiazine (as a polymerization inhibitor), and then internal air of the autoclave was replaced with nitrogen gas, and then the temperature was raised to 60° C. and the internal pressure was adjusted to 1.0 MPa. Next, each of 226 g of ethylene oxide and 336 g of acrylic acid was supplied at an almost constant rate over a period of 2 hours (during this supply, the molar ratio of ethylene oxide/acrylic acid was set in the range of 1.0 to 1.2 (but not including 1.0) and, after the end of the supply, this ratio was 1.1), while 60° C. was kept to carry out a reaction. After the supply of the ethylene oxide and the acrylic acid had been completed, the reaction temperature was kept constant at 60° C. to continue the reaction till the amount of the unreacted acrylic acid (measured by neutralization titration) decreased to 0.10 weight %. As a result of the continuation of the reaction for 4.6 hours, the unreacted acrylic acid decreased to 0.10 weight %, so the reaction liquid was cooled. A gas-chromatographic analysis of the resultant reaction liquid showed a hydroxyethyl acrylate (objective product) concentration of 91 weight %, an ethylene glycol diacrylate (diester) concentration of 0.10 weight %, and a diethylene glycol monoacrylate (diaddition product) concentration of 6.8 weight %.

Next, the resultant reaction liquid was purified in the same way as of Example 1, thus obtaining 626 g of hydroxyethyl acrylate.

A gas-chromatographic analysis of the resultant hydroxyethyl acrylate showed its purity of 97.1 weight % and an ethylene glycol diacrylate (impurity) content of 0.10 weight %, and an analysis by neutralization titration showed an acid component content of 0.06 weight %.

EXAMPLE 4

The reaction was carried out in the same way as of Example 3, and then 1.0 g of salicylic acid was added as a diester inhibitor to the resultant reaction liquid. Thereafter, the purification was carried out in the same way as of Example 1, thus obtaining 626 g of hydroxyethyl acrylate.

A gas-chromatographic analysis of the resultant hydroxyethyl acrylate showed its purity of 97.0 weight % and an ethylene glycol diacrylate (impurity) content of 0.06 weight %, and an analysis by neutralization titration showed an acid component content of 0.06 weight %.

EXAMPLE 5

An SUS-316-made autoclave of 1 L in capacity with a stirrer was charged with 22.6 g of ethylene oxide, 140 g of hydroxyethyl acrylate, 2.10 g of chromium acetate (as a catalyst), and 0.42 g of phenothiazine (as a polymerization inhibitor), and then internal air of the autoclave was replaced with nitrogen gas, and then the temperature was raised to 60° C. and the internal pressure was adjusted to 1.0 MPa. Next, each of 203.4 g of ethylene oxide and 336 g of acrylic acid was supplied at an almost constant rate over a period of 2 hours (during this supply, the molar ratio of ethylene oxide/ acrylic acid was set at not less than 1.1 and, after the end of the supply, this ratio was 1.1), while 60° C. was kept to carry out a reaction. After the supply of the ethylene oxide and the acrylic acid had been completed, the reaction temperature was kept constant at 60° C. to continue the reaction till the amount of the unreacted acrylic acid (measured by neutralization titration) decreased to 0.10 weight %. As a result of the continuation of the reaction for 4.5 hours, the unreacted acrylic acid decreased to 0.10 weight %, so the reaction liquid was cooled. A gas-chromatographic analysis of the resultant reaction liquid showed a hydroxyethyl acrylate (objective product) concentration of 91 weight %, an ethylene glycol diacrylate (diester) concentration of 0.10 weight %, and a diethylene glycol monoacrylate (diaddition product) concentration of 6.9 weight %.

Next, the resultant reaction liquid was purified in the same way as of Example 1, thus obtaining 626 g of hydroxyethyl acrylate.

A gas-chromatographic analysis of the resultant hydroxyethyl acrylate showed its purity of 97.0 weight % and an ethylene glycol diacrylate (impurity) content of 0.10 weight %, and an analysis by neutralization titration showed an acid component content of 0.06 weight %.

EXAMPLE 6

The reaction was carried out in the same way as of Example 5, and then 1.0 g of phthalic acid was added as a diester inhibitor to the resultant reaction liquid. Thereafter, the purification was carried out in the same way as of Example 1, thus obtaining 626 g of hydroxyethyl acrylate.

A gas-chromatographic analysis of the resultant hydroxyethyl acrylate showed its purity of 97.0 weight % and an ethylene glycol diacrylate (impurity) content of 0.06 weight %, and an analysis by neutralization titration showed an acid component content of 0.06 weight %.

EXAMPLE 7

An SUS-316-made autoclave of 1 L in capacity with a stirrer was charged with 240.0 g of ethylene oxide, 0.90 g of chromium acetate (as a catalyst), and 0.45 g of phenothiazine (as a polymerization inhibitor), and then internal air of the autoclave was replaced with nitrogen gas, and then the temperature was raised to 70° C. and the internal pressure was adjusted to 1.0 MPa. Next, 448 g of methacrylic acid was supplied at an almost constant rate over a period of 2 hours (during this supply, the molar ratio of ethylene oxide/ methacrylic acid was set at not less than 1.05 and, after the end of the supply, this ratio was 1.05), while 70° C. was kept to carry out a reaction. After the supply of the methacrylic acid had been completed, the reaction temperature was kept constant at 70° C. to continue the reaction till the amount of the unreacted methacrylic acid (measured by neutralization titration) decreased to 0.10 weight %. As a result of the continuation of the reaction for 3.5 hours, the unreacted methacrylic acid decreased to 0.10 weight %, so the reaction liquid was cooled. A gas-chromatographic analysis of the resultant reaction liquid showed a hydroxyethyl methacrylate (objective product) concentration of 95 weight %, an ethylene glycol dimethacrylate (diester) concentration of 0.05 weight %, and a diethylene glycol monomethacrylate (diaddition product) concentration of 4.2 weight %.

Next, the resultant reaction liquid was purified in the same way as of Example 1, thus obtaining 648 g of hydroxyethyl methacrylate.

A gas-chromatographic analysis of the resultant hydroxyethyl methacrylate showed its purity of 97.8 weight % and an ethylene glycol dimethacrylate (impurity) content of 0.06 weight %, and an analysis by neutralization titration showed an acid component content of 0.03 weight %.

EXAMPLE 8

The reaction was carried out in the same way as of Example 7, and then 0.5 g of maleic acid was added as a diester inhibitor to the resultant reaction liquid. Thereafter, the purification was carried out in the same way as of Example 1, thus obtaining 648 g of hydroxyethyl methacrylate.

A gas-chromatographic analysis of the resultant hydroxyethyl methacrylate showed its purity of 97.8 weight % and an ethylene glycol dimethacrylate (impurity) content of 0.05 weight %, and an analysis by neutralization titration showed an acid component content of 0.03 weight %.

EXAMPLE 9

An SUS-316-made autoclave of 1 L in capacity with a stirrer was charged with 47.9 g of methacrylic acid, 20.0 g of ethylene oxide, 95 g of hydroxyethyl methacrylate, 0.90 g of chromium acetate (as a catalyst), and 0.45 g of phenothiazine (as a polymerization inhibitor), and then internal air of the autoclave was replaced with nitrogen gas, and then the temperature was raised to 70° C. and the internal pressure was adjusted to 1.0 MPa. Next, each of 220 g of ethylene oxide and 400.1 g of methacrylic acid was supplied at an almost constant rate over a period of 2 hours (during this supply, the molar ratio of ethylene oxide/methacrylic acid was set in the range of 0 to 1.0 in a period of from the beginning of the supply till a point of time of 0.6 hour thereafter (30% of the total supplying time) and then in the range of 1.0 to 1.05 (but not including 1.0) in a period of from the above point of time of 0.6 hour till the end of the supply (70% of the total supplying time); and, after the end of the supply, the above ratio was 1.05), while 70° C. was kept to carry out a reaction. After the supply of the ethylene oxide and the methacrylic acid had been completed, the reaction temperature was kept constant at 70° C. to continue the reaction till the amount of the unreacted methacrylic acid (measured by neutralization titration) decreased to 0.10 weight %. As a result of the continuation of the reaction for 4.0 hours, the unreacted methacrylic acid decreased to 0.10 weight %, so the reaction liquid was cooled. A gas-chromatographic analysis of the resultant reaction liquid showed a hydroxyethyl methacrylate (objective product) concentration of 95 weight %, an ethylene glycol dimethacrylate (diester) concentration of 0.07 weight %, and a diethylene glycol monomethacrylate (diaddition product) concentration of 4.5 weight %.

Next, the resultant reaction liquid was purified in the same way as of Example 1, thus obtaining 648 g of hydroxyethyl methacrylate.

A gas-chromatographic analysis of the resultant hydroxyethyl methacrylate showed its purity of 97.8 weight % and an ethylene glycol dimethacrylate (impurity) content of 0.08 weight %, and an analysis by neutralization titration showed an acid component content of 0.03 weight %.

EXAMPLE 10

The reaction was carried out in the same way as of Example 9, and then 0.7 g of salicylic acid was added as a diester inhibitor to the resultant reaction liquid. Thereafter, the purification was carried out in the same way as of Example 1, thus obtaining 648 g of hydroxyethyl methacrylate.

A gas-chromatographic analysis of the resultant hydroxyethyl methacrylate showed its purity of 97.8 weight % and an ethylene glycol dimethacrylate (impurity) content of 0.07 weight %, and an analysis by neutralization titration showed an acid component content of 0.03 weight %.

Comparative Example 1

An SUS-316-made autoclave of 1 L in capacity with a stirrer was charged with 420 g of acrylic acid, 2.10 g of chromium acetate (as a catalyst), and 0.42 g of phenothiazine (as a polymerization inhibitor), and then internal air of the autoclave was replaced with nitrogen gas, and then the temperature was raised to 60° C. and the internal pressure was adjusted to 1.0 MPa. Next, 282 g of ethylene oxide was supplied at a constant rate (0.55 mol/hr) over a period of 2 hours (during this supply, the molar ratio of ethylene oxide/acrylic acid was set in the range of 0 to 1.0 in a period of from the beginning of the supply till a point of time of 1.8 hours thereafter (90% of the total supplying time) and then in the range of 1.0 to 1.1 (but not including 1.0) in a period of from the above point of time of 1.8 hours till the end of the supply (10% of the total supplying time); and, after the end of the supply, the above ratio was 1.1), while 60° C. was kept to carry out a reaction. After the supply of the ethylene oxide had been completed, the reaction temperature was kept constant at 60° C. to continue the reaction till the amount of the unreacted acrylic acid (measured by neutralization titration) decreased to 0.10 weight %. As a result of the continuation of the reaction for 5.5 hours, the unreacted acrylic acid decreased to 0.10 weight %, so the reaction liquid was cooled. A gas-chromatographic analysis of the resultant reaction liquid showed a hydroxyethyl acrylate (objective product) concentration of 91 weight %, an ethylene glycol diacrylate (diester) concentration of 0.38 weight %, and a diethylene glycol monoacrylate (diaddition product) concentration of 7.5 weight %.

Next, the resultant reaction liquid was purified in the same way as of Example 1, thus obtaining 626 g of hydroxyethyl acrylate.

A gas-chromatographic analysis of the resultant hydroxyethyl acrylate showed its purity of 96.7 weight % and an ethylene glycol diacrylate (impurity) content of 0.40 weight %, and an analysis by neutralization titration showed an acid component content of 0.06 weight %.

Comparative Example 2

The reaction was carried out in the same way as of Comparative Example 1, and then 0.8 g of maleic acid was added as a diester inhibitor to the resultant reaction liquid. Thereafter, the purification was carried out in the same way as of Example 1, thus obtaining 626 g of hydroxyethyl acrylate.

A gas-chromatographic analysis of the resultant hydroxyethyl acrylate showed its purity of 96.8 weight % and an ethylene glycol diacrylate (impurity) content of 0.25 weight %, and an analysis by neutralization titration showed an acid component content of 0.06 weight %.

Comparative Example 3

The reaction was carried out in the same way as of Comparative Example 1, and then the resultant reaction liquid was purified under the same distillation conditions as of Example 1 and in a shorter time than that in Example 1, thus obtaining 346 g of hydroxyethyl acrylate.

A gas-chromatographic analysis of the resultant hydroxyethyl acrylate showed its purity of 98.1 weight % and an ethylene glycol diacrylate (impurity) content of 0.39 weight %, and an analysis by neutralization titration showed an acid component content of 0.05 weight %.

Comparative Example 4

The reaction was carried out in the same way as of Comparative Example 1 except to continue the reaction till the amount of the unreacted acrylic acid (measured by neutralization titration) decreased to 0.80 weight %. Specifically, as a result of the continuation of the reaction for 5.0 hours after the completion of the supply of the ethylene oxide, the unreacted acrylic acid decreased to 0.80 weight %, so the reaction liquid was cooled. A gas-chromatographic analysis of the resultant reaction liquid showed a hydroxyethyl acrylate (objective product) concentration of 91 weight %, an ethylene glycol diacrylate (diester) concentration of 0.10 weight %, and a diethylene glycol monoacrylate (diaddition product) concentration of 6.9 weight %.

Next, the resultant reaction liquid was purified in the same way as of Example 1, thus obtaining 626 g of hydroxyethyl acrylate.

A gas-chromatographic analysis of the resultant hydroxyethyl acrylate showed its purity of 96.6 weight % and an ethylene glycol diacrylate (impurity) content of 0.21 weight %, and an analysis by neutralization titration showed an acid component content of 0.40 weight %.

Comparative Example 5

An SUS-316-made autoclave of 1 L in capacity with a stirrer was charged with 47.7 g of methacrylic acid, 110 g of hydroxyethyl methacrylate, 0.90 g of chromium acetate (as a catalyst), and 0.45 g of phenothiazine (as a polymerization inhibitor), and then internal air of the autoclave was replaced with nitrogen gas, and then the temperature was raised to 70° C. and the internal pressure was adjusted to 1.0 MPa. Next, each of 400.3 g of methacrylic acid and 240 g of ethylene oxide was supplied at an almost constant rate over a period of 2 hours (during this supply, the molar ratio of ethylene oxide/methacrylic acid was set in the range of 0 to 1.0 in a period of from the beginning of the supply till a point of time of 1.4 hours thereafter (70% of the total supplying time) and then in the range of 1.0 to 1.05 (but not including 1.0) in a period of from the above point of time of 1.4 hours till the end of the supply (30% of the total supplying time); and, after the end of the supply, the above ratio was 1.05), while 70° C. was kept to carry out a reaction. After the supply of the methacrylic acid and the ethylene oxide had been completed, the reaction temperature was kept constant at 70° C. to continue the reaction till the amount of the unreacted methacrylic acid (measured by neutralization titration)

decreased to 0.10 weight %. As a result of the continuation of the reaction for 5.0 hours, the unreacted methacrylic acid decreased to 0.10 weight %, so the reaction liquid was cooled. A gas-chromatographic analysis of the resultant reaction liquid showed a hydroxyethyl methacrylate (objective product) concentration of 95 weight %, an ethylene glycol dimethacrylate (diester) concentration of 0.18 weight %, and a diethylene glycol monomethacrylate (diaddition product) concentration of 4.5 weight %.

Next, the resultant reaction liquid was purified in the same way as of Example 1, thus obtaining 648 g of hydroxyethyl methacrylate.

A gas-chromatographic analysis of the resultant hydroxyethyl methacrylate showed its purity of 97.6 weight % and an ethylene glycol dimethacrylate (impurity) content of 0.20 weight %, and an analysis by neutralization titration showed an acid component content of 0.03 weight %.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for a hydroxyalkyl (meth)acrylate, which comprises the steps of:
    a) carrying out a batch reaction in a reactor between an alkylene oxide and (meth)acrylic acid in the presence of a catalyst in order to produce the hydroxyalkyl (meth)acrylate;
    b) defining a supply time period as a time period during which alkylene oxide and/or (meth)acrylic acid are being supplied into said reactor while content inside said reactor has a temperature of not lower than 40° C.;
    c) defining a molar ratio time period as a time period during which a molar ratio of alkylene oxide, which has been introduced into said reactor, to (meth)acrylic acid, which has been introduced into said reactor, is more than 1.0; and
    d) adjusting a supplying of alkylene oxide and/or (meth)acrylic acid into said reactor such that the molar ratio time period is not less than 40% of the supply time period.

2. A production process for a hydroxyalkyl (meth)acrylate according to claim 1, which further comprises the step of adding a diester inhibitor after the batch reaction.

3. A production process for a hydroxyalkyl (meth)acrylate according to claim 1, which further comprises the steps of: initially charging the alkylene oxide and/or a hydroxyalkyl (meth)acrylate into the reactor; and then beginning to supply the (meth)acrylic acid.

4. A production process for a hydroxyalkyl (meth)acrylate according to claim 2, which further comprises the steps of: charging the alkylene oxide and/or a hydroxyalkyl (meth)acrylate into the reactor; and then beginning to supply the (meth)acrylic acid.

5. A production process for a hydroxyalkyl (meth)acrylate, which comprises the steps of:
    a) carrying out a batch reaction in a reactor between an alkylene oxide and (meth)acrylic acid in the presence of a catalyst in order to produce the hydroxyalkyl (meth)acrylate;
    b) initially charging said reactor with at least one of alkylene oxide, (meth)acrylic acid, and hydroxyalkyl (meth)acrylate;
    c) supplying alkylene oxide and/or (meth)acrylic acid into said reactor while content inside said reactor has a temperature of not lower than 40° C., wherein said step of supplying occurs after said step of initially charging, wherein said step of supplying occurs during a time period defined as a supply time period;
    d) attaining a molar ratio of alkylene oxide, which has been introduced into said reactor, to (meth)acrylic acid, which has been introduced into said reactor, of more than 1.0, and defining a molar ratio time period as a time period during which said molar ratio is more than 1.0; and
    e) adjusting amounts of alkylene oxide and/or (meth)acrylic acid supplied into said reactor during said step of supplying such that the molar ratio time period is not less than 40% of the supply time period.

* * * * *